United States Patent [19]

DeVries et al.

[11] 4,316,385
[45] Feb. 23, 1982

[54] FINGERPRINTING CRYSTALS

[75] Inventors: Robert C. DeVries, Saratoga; Roy E. Tuft, Albany, both of N.Y.

[73] Assignee: General Electric Company, Schenectady, N.Y.

[21] Appl. No.: 160,464

[22] Filed: Jun. 18, 1980

[51] Int. Cl.³ .............................................. G01N 19/08
[52] U.S. Cl. ........................................ 73/104; 356/30
[58] Field of Search .............. 73/104, 432 R; 356/30, 356/32; 204/157.1 H

[56] References Cited

U.S. PATENT DOCUMENTS 4,143,544 3/1979 DeVries et al. ...................... 73/104
4,200,506 4/1980 Dreschhoff et al. ......... 204/157.1 H

OTHER PUBLICATIONS

Large et al., Journal of Materials Science, vol. 2, (1967), pp. 589–609, "Ion-Implantation Doping of Semiconductors".
Chemical Abstracts, vol. 77, 54910e.

*Primary Examiner*—Anthony V. Ciarlante
*Attorney, Agent, or Firm*—Jane M. Binkowski; James C. Davis, Jr.; Joseph T. Cohen

[57] ABSTRACT

A smooth surface of a diamond or cubic boron nitride crystal is bombarded with ions sufficiently to penetrate the surface and impart an ion implanted region in the crystal in a predetermined pattern, the resulting crystal is charged electrostatically, and a powder is applied to the charged smooth surface producing a pattern thereon which is a delineation of the implanted region and can be used to identify or fingerprint the crystal.

12 Claims, 4 Drawing Figures

FINGERPRINTING CRYSTALS

The present invention relates to characterizing or fingerprinting diamond or cubic boron nitride crystal enabling its identification thereafter.

U.S. Pat. No. 4,143,544 to DeVries et al, which is incorporated herein by reference and which is assigned to the assignee herein, discloses a method for revealing structural growth discontinuities of a crystal. Specifically, in U.S. Pat. No. 4,143,544 inhomogeneities in diamond and cubic boron nitride could be revealed by electrostatic charging of the crystal followed by an application of a fine powder or "dust" to reveal the charged regions. These are revealed because the presence of regions of different conductivity causes the surface of the crystal to be charged differently. The structure that is revealed is dependent on the "grown-in" inhomogeneities and as a result a very homogeneous crystal will now show a pattern. When the inhomogeneous regions are present and can be revealed, a truly unique fingerprint of the crystal exists.

Specifically, U.S. Pat. No. 4,143,544 claims a process for characterizing a crystal selected from the group consisting of natural diamond, synthetic diamond and cubic boron nitride, said crystal containing at least a significant amount of structural growth discontinuities caused by fluctuations in the conditions contacting the growing crystal which comprises providing said crystal with at least one external surface having a surface area of at least 0.1 square millimeter which is at least substantially smooth and without significant elevational differences and which intersects at least a portion of said growth discontinuities, electrostatically charging said crystal so that at least said smooth surface of crystal is electrostatically charged, applying a powder to said charged surface forming a powder pattern on said charged surface, said powder having a particle size ranging from submicron to about 45 microns, said pattern being a delineation of said intersected growth discontinuities.

However, there are some natural diamond crystals which grew under such homogeneous conditions that no growth discontinuities are present, and for such crystals U.S. Pat. No. 4,143,544 is not operable. Also, U.S. Pat. No. 4,143,544 is not useful for crystals where growth discontinuities may be present but a suitable surface intersecting such growth discontinuities is not present, of where the difference in electrical conductivity between regions in the crystal is not sufficient to delineate.

The present process for fingerprinting crystals is directed to crystals with no growth discontinuities as well as those with growth discontinuities. Specifically, in the present process, diamond crystals, natural as well as synthetic, and cubic boron nitride crystals are subjected to ion implantation sufficient to impart to them a characteristic structure. Although prior art has subjected diamond crystals to ion implantation, such prior art normally caused some obvious visible damage to the appearance of the crystal, and also such ion implantation was carried out to make the crystal semiconductive, usually after a subsequent annealing step. In contrast, the present invention does not visibly damage the appearance of the crystal and is carried out to provide the crystal with a preselected characteristic or fingerprinting structure sufficient to be revealed by the present powder dusting technique on any smooth surface of the crystal that has been subjected to ion bombardment.

Specifically, in the present invention, since the development of dust patterns is related to the presence of adjacent regions of different conductivity, such regions are purposely put in the crystal by ion implantation or bombardment in a known pattern (geometric design, initials, numbers, etc.) through a mask. The establishment of regions of different conductivity by this technique subsequently is revealed by electrostatic charging and dusting.

Briefly stated, the present process comprises selectively bombarding at least a smooth surface of a diamond or cubic boron nitride crystal with preselected implanting ions sufficiently to penetrate said smooth surface of the crystal and impart a predetermined characteristic structure thereto without any significant deleterious effect on the appearance of the crystal, electrostatically charging the resulting characterized crystal, and applying a powder to the charged smooth surface producing a pattern thereon which is a delineation of the characterizing structure.

Specifically, the present invention is a process for characterizing a crystal selected from the group consisting of natural diamond, synthetic diamond and cubic boron nitride by implanting ions therein which impart to said crystal a predetermined structure which comprises providing said crystal with at least one external surface having a surface area of at least 0.1 square millimeter which is at least substantially smooth and without significant elevational differences, positioning said crystal in a chamber for ion-bombardment of at least said smooth surface thereof, providing said chamber with ionizing means for producing ions in beam form and means for accelerating the resulting implanting ions, evacuating said chamber, providing said chamber with a material to be ionized to produce implanting ions, sufficiently ionizing said material forming and accelerating a beam of the resulting implanting ions to selectively penetrate at least said smooth surface of said crystal to impart a predetermined structure thereto without significant deleterious damage to the appearance of said crystal, said chamber having been evacuated sufficiently to be free of at least significant contaminants, electrostatically charging the resulting characterized crystal so that at least said smooth surface of said crystal is electrostatically charged, applying a powder to said charged surface forming a powder pattern on said charged surface, said powder ranging in particle size from submicron to about 45 microns, said pattern being a delineation of the ion-implanted structure in said crystal.

The product of the present invention is a fingerprint of a crystal selected from the group consisting of natural diamond, synthetic diamond and cubic boron nitride, said crystal having at least one external surface with a surface area of at least 0.1 square millimeter which is at least substantially smooth and which is associated with the ion-implanted structure, said fingerprint being composed of a powder pattern which is a delineation of said ion-implanted structure produced by the present process.

Those skilled in the art will gain a further and better understanding of the present invention from the figures accompanying and forming part of the specification, in which.

Figure 1:
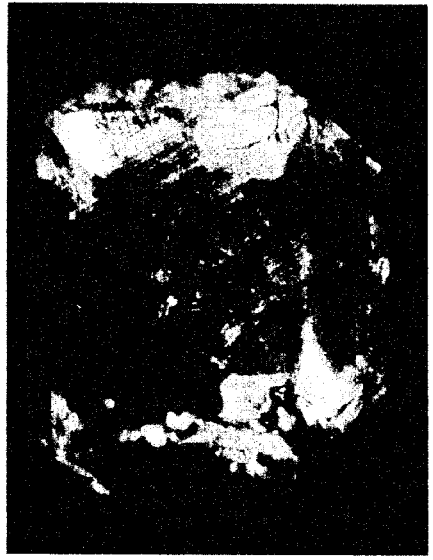
FIG. 1(a) is a photomicrograph (magnified about 14×) of a synthetic diamond crystal showing a flat, smooth surface, i.e. (100) face, which had been implanted with a horizontal band of boron ions and a vertical band of phosphorus ions in accordance with the present invention.
FIG. 1(b) is a photomicrograph (magnified about 14×) of the crystal of FIG. 1(a), electrostatically charged and dusted with powder and showing the bands of the implanted boron and phosphorus ions.
FIG. 1(c) is a photomicrograph (magnified about 14×) of the crystal of FIG. 1(a), electrostatically charged negatively and dusted with powder and showing the horizontal band due to boron ion implantation.
FIG. 1(d) is a photomicrograph (magnified about 14×) of FIG. 1(a), electrostatically charged positively and dusted with powder and showing the vertical band due to phosphorus ion implantation.
Figure 1:
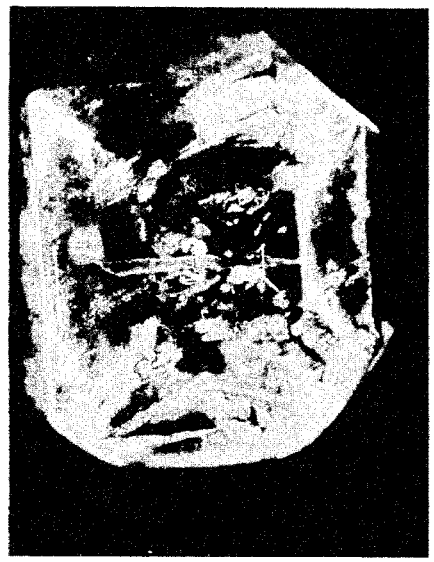
Figure 1:
Figure 1:

In carrying out the present process, the diamond or cubic boron nitride crystal should have at least one surface for producing a powder pattern, and preferably a plurality of such surfaces. Specifically, the crystal should have at least one surface which is an external, i.e. outside, surface with an area of at least 0.1 square millimeter, and preferably larger, which is smooth or at least substantially smooth, and which is free of elevational differences or at least substantially free of elevational differences. This external surface may be a curved or convex surface, but preferably for ion bombardment and easier recording of the powder pattern, it is a flat surface, and most preferably, it is a flat, totally level, plane surface. There is no maximum limit on the surface area of the present pattern-producing surface of the crystal. Also, there is no maximum limit on the size of the crystal except perhaps that imposed by size limitation of the ion implantation apparatus.

It may be necessary to shape at least one surface of the crystal of natural or synthetic diamond or synthetic cubic boron nitride to provide it with the desired smooth surface. By shaping, it is meant herein, for example, abrading or polishing or any such technique. Also, the crystal can be shaped by grinding usually by means of a diamond impregnated grinding wheel. A smooth polished surface can be produced mechanically by polishing the crystal on a cast iron lap or scaife. After mechanical polishing, the crystal should be cleaned with solvent such as acetone or isopropyl alcohol and dried to remove any adherent particles or dust which may interfere with the present powder pattern formation.

In an octahedron shaped diamond crystal the maximum flat area would be on the (100) plane through the girdle of the octahedron. In the practice of diamond gemstone production from naturally occurring octahedra, it is common to saw on the (100) plane somewhat above the girdle so as to produce one larger and one smaller stone from the same original crystal. The cut (100) type surfaces of the resulting crystals become the large table facet of a brilliant cut and are nearly ideal pattern-producing surfaces.

The present ion-implantation process can be carried out by a number of techniques and can be carried out by commercially available ion beam-implantation apparatus. Generally, such apparatus is comprised of means, such as an electron gun, for ionizing material and forming a beam of the resulting desired ions, and accelerating means, such as linear accelerator or cyclotron, to provide the beam with the required velocity. The means for ionizing the material can produce positive or negative ions which are formed from a neutral atom or molecule, i.e. the material to be ionized, by the action of an ionizing system such as radiation. For example, the material to be ionized can be passed into a chamber in gaseous or vapor form and bombarded by electrons at high energy which dissociate and ionize the atoms, and a beam formed of the desired resulting implanting ions, which may require a mass-analyzing magnet for separating the implanting ions, as well as means for focusing such ion beam. The beam of ions to be implanted is subjected to an accelerator to give it a velocity, determinable empirically in the present process, sufficient to penetrate the smooth surface of the crystal, i.e. it should not cause any significant deleterious damage to the appearance of the crystal.

In the present process any material which on being ionized produces the desired implanting ions is useful. The implanting ions should be able to penetrate the smooth surface which is to be the pattern-producing surface of the crystal without causing any significant deleterious damage to its appearance. The required velocity or acceleration of the implanting ions is determinable empirically. In principle, the implanting ions can be positive or negative, but usually ion implantation apparatus is designed to accelerate positive ions only. Specifically, ions produced from a single source material can be implanted in a crystal in any configuration desired to impart the characterizing structure which will produce the desired powder-pattern or fingerprint.

Representative of the implanting ions are those of carbon, boron and phosphorous. The preferred ions are generally small. However, there is no limitation on the particular ion or combination of ions used if such ions can be implanted in a crystal without any significant deleterious damage to the appearance of the crystal.

Where different, i.e. a combination of, ions are implanted in the crystal, generally such ions react differently to the sign of the charge of the electrostatic field. For example, if the crystal is implanted with ions of boron and phosphorous in accordance with the present invention, and then electrostatically charged and dusted with powder, the implanted boron ions will charge differently from the phosphorous ions and will reveal an image or dust pattern different from that of the phosphorous ions.

Ordinarily, in carrying out the present invention, it is necessary to mask portions of the crystal to be protected from ion implantation to produce the desired predetermined powder pattern or fingerprint of the crystal. Useful mask materials include silicon dioxide, vapor deposited coating of metal or separate metal masks such as foils of aluminum or copper. However, under controlled conditions, a beam of ions of very small area can be made to impart the desired characterization to the crystal without masking the crystal.

The present process can be carried out at any temperature which does not have a significantly deleterious effect on the diamond or cubic boron nitride cyrstal. Normally, it is carried out at room or ambient temperature.

The characterizing powder pattern produced in the present invention depends largely on the configuration of the implanted ions. In those instances where a pattern-producing surface intersects growth discontinuities of the crystal, there will be additional characterizing pattern produced from such growth discontinuities. However, in the present invention, the implantation of ions to produce a desired powder pattern is sufficient to fingerprint or characterize the crystal even on external growth surfaces where no growth discontinuities are present.

When required, the pattern-producing surface or surfaces of a crystal produced by the present ion-implantation can be determined empirically. For example, the entire crystal can be charged electrostatically, the present fine powder applied or dusted onto the charged crystal and the particular surface or surfaces of the charged crystal on which the fingerprinting or powder pattern forms determined.

In carrying out the present process, the crystal is electrostatically charged at least sufficiently to produce a powder pattern in accordance with the present process. Preferably, before the crystal is electrostatically charged, it is cleaned with solvent such as acetone or isopropyl alcohol and dried to remove any adherent particles and dust which may interfere with the present powder-pattern formation. The crystal can be electrostatically charged so that at least the patternforming surface of the crystal is charged, but preferably, the entire crystal is electrostatically charged.

The crystal can be electrostatically charged by a number of techniques. In one technique, the crystal is rubbed with an insulating material. By an insulating material it is meant a material which permits the passage of the lines of force of an electrostatic field but does not conduct electric current. Preferably, the insulating material is a continuous pliable material. Representative of the insulating materials useful in the present process are cotton cloth, silk, paper, rubber and plastics.

In another technique, the crystal is electrostatically charged by pressing an adhesive surface of tape on it and stripping it off rapidly. This technique also can serve as a simultaneous cleaning process for the surface to be studied.

Preferably, the crystal is charged electrostatically by subjecting it to an electric field. For example, the crystal can be placed in an electric field provided by a corona discharge, which is an electric discharge resulting from a partial electric breakdown in the gas or air surrounding a wire at high potential.

The powder used to form the pattern in the present process, i.e. the pattern-forming powder, can be an insulating powder, semiconducting or metallic, or mixtures thereof. Representative of these powders are talc, flour, polymer, $Al_2O_3$, $ZnS$, $Pb_3O_4$, $CrO_2$, $Fe_2O_3$, $Cr_2O_3$, nickel, iron, and graphite.

The pattern-forming powder should be non-aggregative in order that it may form reproducible patterns of satisfactory resolution. Usually the smaller the particle size of the powder, the more refined is the resolution of the resulting pattern. For best results the powder has a particle size ranging from submicron to about 5 microns. However, powder comprised of a mixture of sizes ranging up to about 45 microns may also be used providing at least about 5% by volume, and preferably higher portions of such a powder, is composed of particles ranging from submicron to about 10 microns in size. The large particles do not give good resolution and may not stick. In a mixed particle size powder the finer sizes tend to be the pattern producing particles.

The present powder can be applied to the charged crystal by a number of techniques. For example, it can be sprinkled or dusted onto the charged crystal by means of, for example, a salt shaker, blower, or syringe. The powder is applied at least to the entire charged pattern-producing surface, but preferably, it is applied to the entire exposed surface area of the charged crystal. For example, if the crystal is mounted in a ring or some type of holder, the powder is applied preferably to the entire exposed external surface area of the crystal. It appears that the implanted ions within the charged crystal create regions of conductivity different from the matrix thereby, after charging, attracting the powder forming it into a powder pattern. Alternatively, the charged crystal can be dipped into the powder, and the excess powder shaken off or otherwise removed to reveal a powder pattern. In another technique, a fast-drying liquid dispersion of the powder can be sprayed or otherwise deposited on the charged crystal forming a wet coating thereon, which as it dries, frees the dry powder to form into a pattern on the charged crystal.

The powder forming the pattern on the charged crystal clings to it apparently being held in place by charged forces of the crystal. Excess powder which may deposit on the crystal, i.e. powder which does not form a part of the powder pattern, does not show this clinging effect, and since there is no attraction between it and the crystal, it can be removed by a number of techniques without affecting the powder pattern. For example, it can be gently blown off or shaken off the charged crystal. If desired, excess powder can be removed from the charged crystal by placing the charged crystal within a stream of air flowing at a rate sufficient to remove or carry off the excess powder but not so high a rate as to have any effect on the powder pattern.

In one embodiment of the present invention, the crystal is electrostatically charged and the powder is applied thereto simultaneously, i.e. the powder-pattern is developed at the same time the crystal is being charged. For example, while the crystal is being electrostatically charged in a corona discharge, the powder can be sprayed or otherwise applied to the crystal. This is an advantage if conditions are such that rapid leakage of the charge might take place, such as under high humidity, between the charging and dusting steps.

In yet another embodiment the crystal is electrostatically charged in a positive or negative field produced by ionization of air molecules by corona discharge. As a result, the pattern-producing surface of the resulting charged crystal may be positively charged or negatively charged. When powder is applied according to the present process to a crystal with pattern-producing surfaces which are positively charged, and subsequently applied to the same crystal with the pattern-producing surfaces negatively charged, the resulting powder patterns bear a relationship to each other that is similar to positive and negative photographic prints. The patterns are geometrically the same but the concentrations of the powder is reversed. Such a combination of patterns is also unique to each crystal.

Where different ions are implanted in the crystal, such ions may react differently to the sign of the charge of the electrostatic field. For example, if the crystal is implanted with boron ions, it will charge differently than an area that has been implanted with phosphorous ions.

Also, some powders have a tendency to be positively charged and others have a tendency to be negatively charged. Thus, the powder pattern produced by one powder on a positively charged surface of a crystal can be the same as the powder pattern produced by another powder on the same surface of the crystal but negatively charged, indicating that the powders are oppositely charged initially, and in such instance the concentration of a powder in a pattern will be a function of both the sign of the charge on the crystal surface and on the particles.

Since many powders frequently have a tendency to be composed of a mixture of positively charged and negatively charged particles, an electric field is useful in the present process to produce patterns of high resolution by passing such a powder, usually in the form of a dust cloud, through the electric field prior to deposition on the charged crystal. The field extracts particles from the dust cloud of charge opposite to it. For example, the electrode for establishing the electric field may be in the form of a metallic screen located close to and under the mounted crystal providing the field between it and the crystal and the powder is passed through the screen and through the field to deposit on the charged crystal. Specifically, when the crystal is positively charged, the electrode would be negatively charged providing a negatively charged field to remove particles of positive charge from the dust cloud leaving particles of negative charge to deposit on the positively charged surfaces of the crystal. Under these conditions the particles of negative charge may be further charged and accelerated by the field to deposit on the crystal. The powder pattern on the crystal is enhanced by the resulting increase in the proportion of particles of negative charge.

The powder pattern produced by the present process can be recorded by a number of techniques. For example, it can be recorded photographically. It is also possible to preserve and record the present powder pattern by placing a piece of transparent adhesive tape, for example Scotch tape, over the pattern. When pressed down smoothly, the powder pattern is removed and preserved by the tape when it is stripped off the crystal. The tape can then be placed on a card or rigid surface or on another piece of tape for preservation. If the card or surface is transparent it is easier to make comparisons of patterns by overlay on a light box or by projection onto a screen.

The powder pattern formed in accordance with the present process is recorded so that it is available for comparison with subsequently formed powder patterns. Powder patterns produced by the present process can be compared by a number of techniques. For example, a powder pattern produced in the same manner on the same powder-producing surface or surfaces of the same crystal as a recorded powder pattern should be the same or at least sufficiently or substantially the same as the recorded powder pattern so as to identify the particular crystal. Alternatively, identification of the crystal can be made by such comparison of the powder patterns along with their location or orientation with respect to some part or the rest of the crystal. Specifically, comparison can be made by comparing photographs of the powder pattern-carrying crystals. Alternatively comparisons can be made visually, preferably under a microscope. Also, comparisons can be made by superimposing one powder pattern onto another. Projection of the powder patterns on a wall magnifies them substantially and produces projected patterns of high resolution.

A fluorescent or colored powder aids in seeing the patterns on the crystal surface. Specifically, it is particularly preferred to use a powder of a color which gives a contrasting color when deposited on a crystal of a particular color, i.e. or opaque on a transparent crystal.

The present invention is useful in characterizing abrasive grain as well as gemstones. The present process is non-destructive to the crystal or to the polished surface of the crystal and a spray or powder pattern of the table of a gem diamond would be like a fingerprint—no two alike.

The invention is further illustrated by the following examples where the procedure was as follows unless otherwise noted:

All polishing of the crystal was carried out mechanically on an iron scaife.

In each instance before electrostatically charging a crystal, the crystal was cleaned to remove any powder or dust which might be present on its surfaces. To clean the crystal it was dipped or swabbed in acetone or isopropyl alcohol and dried in air or in jet of air or inert gas.

The powder used was comprised of nickel powder suspended in an insulating liquid, i.e. a trichlorofluoroalkane, under pressure and sold under the trademark Kyread. This was a suspension which dried rapidly, usually from less than a second to 2 seconds after application. Examination of the resulting dry nickel powder showed it to be non-aggregative and free-flowing. The nickel powder ranged in size from about $\frac{1}{2}$ micron to about 1 micron.

All of the examples were carried out at room temperature in air.

The smooth surface of the crystal used as a powder pattern producing surface was greater than 0.1 square millimeter and had no significant elevational differences.

A commercially available ion-implantation apparatus was used.

Electrostatic charging was carried out at room temperature by rubbing the crystal with an insulating material such as cloth, and dusting the resulting charged crystal with powder to reveal the pattern formed thereon. The powder was then removed and the crystal was recharged with a commercially available electric charging device, i.e. an electrostatic gun, and the resulting electrostatically charged crystal was dusted with powder to reveal the pattern formed thereon.

EXAMPLE 1

A thin square slab of colorless type IIa synthetic diamond crystal about 3 mm×3 mm×$\frac{1}{2}$ mm was first electrostatically charged and then dusted to reveal the "as-grown" pattern on two opposite (100) type faces. These original patterns were photographed. The crystal was then cleaned and masked with Al foil to expose a narrow band approximately across one side of the crystal surface. The carbon ion implantation was carried out in a vacuum of about $5 \times 10^{-7}$ torr at room temperature. The crystal was offset 7° to the beam to minimize channeling effects. Specifically, one face of the crystal slab was exposed to known ion fluences and energies. This procedure was then repeated with the crystal slab masked at approximately right angles to the previous band. The procedure was again repeated on the opposite face of the crystal and a range of conditions for carbon ion implantation was established for this type IIa diamond crystal. After the ion implantation, the crystal surfaces were charged electrostatically, dusted, and the patterns compared with the patterns produced originally on the crystal before ion implantation. The results are shown in Table I.

TABLE I

| Run | Fluence (carbon) (ions cm$^{-2}$) | Kev | Surface Damage | Dust Pattern |
| --- | --- | --- | --- | --- |
| 1 | $1 \times 10^{14}$ | 350 | yes | yes |
| 2 | $1 \times 10^{13}$ | 350 | no | yes |
| 3 | $5 \times 10^{12}$ | 350 | no | yes |
| 4 | $1 \times 10^{12}$ | 350 | no | doubtful |

Runs 2 and 3 of Table I illustrate the present invention. With the exception of the lowest ion fluence, Run 1, a new clear band in addition to the original charged pattern could be seen after charging and dusting. The new band is invisible without the charging-dusting procedure. In Run 4, the highest dose ($1\times10^{14}$ ions cm$^{-2}$) damaged the crystal visibly and was not useful. Such damage, which is of the order of $R=3680$ Å ($\Delta R_P=344$ Å) would have to be removed by polishing to restore the original beauty of the crystal.

EXAMPLE 2

The procedure used in this example was substantially the same as set forth in Example 1, except that a yellow synthetic diamond Type Ib crystal was used. The crystal had two smooth surfaces, one of which was a (100) surface formed by polishing intersected growth discontinuities in the structure and the second a (100) as-grown surface. No charged dust pattern i.e., fingerprint, could be formed on the as-grown surface because apparently, it does not intersect a region of discontinuity within the crystal.

In each run of Table II, both faces of the crystal were implanted with carbon ions, the crystal was then electrostatically charged and dusted with powder. The results are shown in Table II.

TABLE II

| Run | Fluence (ions cm$^{-2}$) | Kev | Surface Damage | Fingerprinting Dust Pattern |
| --- | --- | --- | --- | --- |
| 5 | $1 \times 10^{13}$ | 350 | no | yes |
| 6 | $1 \times 10^{13}$ | 200 | no | yes |

Runs 5 and 6 illustrate the present invention. There was no visible damage to the crystal, i.e., the crystal did not show any significant deleterious damage. Characterizing dust patterns, i.e., a fingerprint, was formed on each of the (100) faces of the crystal.

EXAMPLE 3

The procedure used in this example was substantially the same as set forth in Example 2 except that a natural colorless octahedron type Ia crystal was used.

The crystal had eight different (111) smooth as-grown surfaces, four of which were subjected to ion implantation. In each run of Table III, one of the surfaces was implanted with carbon ions. After each run, the crystal was electrostatically charged and the respective bombarded surface dusted with powder. The results are given in Table III.

TABLE III

| Run | Fluence (ions cm$^{-2}$) | Kev | Surface Damage | Dust Pattern |
| --- | --- | --- | --- | --- |
| 7 | $1 \times 10^{13}$ | 350 | no | yes |
| 8 | $1 \times 10^{12}$ | 400 | no | no |
| 9 | $1 \times 10^{13}$ | 350 | no | yes |
| 10 | $1 \times 10^{12}$ | 400 | no | no |

Runs 7 and 9 illustrate the present invention and showed fingerprints, i.e. characterizing powder patterns, on their respective bombarded surfaces.

In Runs 8 and 10, the ion implant dose was insufficient to impart a characteristic structure.

EXAMPLE 4

The procedure used in this example was substantially the same as that set forth in Example 1 except that a synthetic Type IIa diamond crystal was used and ions of both boron and phosphorus were implanted in the crystal.

A (100) smooth polished surface was bombarded with ions of boron and then with phosphorus at a fluence of $1\times10^{13}$ ion/cm$^2$ and kev of 350. Specifically, portions of the crystal were masked with Al foil and ions of boron and phosphorus were implanted in separate bands at right angles to each other across the (100) surface of the crystal. This surface was about 5 mm $\times$ 4 mm.

The appearance of the crystal was unchanged after bombardment as shown in FIG. 1(a).

The crystal was then rubbed with cloth to charge the ion-implanted surface and such charged surface dusted with powder. Both bands of the implanted boron and phosphorous ions could be seen simultaneously as shown in FIG. 1(b). Specifically, FIG. 1(b) shows the X-pattern composed of the two separate ion-implanted regions which do not collect dust with this type of charging.

The crystal was then electrostatically charged with an electrostatic charging gun, and it was discovered that each group of implanted ions could be revealed individually and separately by charging the surface with opposite sign using the gun. Specifically, the crystal was electrostatically charged negatively with an electrostatic charging gun, dusted with powder and the boron band was revealed on the surface as shown by FIG. 1(c). Specifically, FIG. 1(c) shows the horizontal band due to boron ion implantation.

The crystal was then electrostatically charged positively with the electrostatic gun, dusted with powder and the vertical band due to phosphorus ion implantations was revealed as shown by FIG. 1(d). Some "grown-in" structures of the crystal was also revealed by this charging mode.

It is obvious that various combinations of the variables could be used for fingerprinting of gemstones.

What is claimed is:

1. A process for fingerprinting a crystal selected from the group consisting of natural diamond, synthetic diamond and cubic boron nitride by implanting ions therein which impart to said crystal a predetermined structure which comprises providing said crystal with at least one external surface having a surface area of at least 0.1 square millimeter which is at least substantially smooth and without significant elevational differences, positioning said crystal in a chamber for ion-bombardment of at least said smooth surface thereof, providing said chamber with ionizing means for producing ions in beam form and means for accelerating the resulting implanting ions, evacuating said chamber, providing said chamber with a material to be ionized to produce implanting ions, sufficiently ionizing said material forming and accelerating a beam of the resulting implanting ions to selectively penetrate at least said smooth surface of said crystal to impart a predetermined structure thereto without significant deleterious damage to the appearance of said crystal, said chamber having been evacuated sufficiently to be free of at least significant contaminants, electrostatically charging the resulting characterized crystal so that at least said smooth surface of said crystal is electrostatically charged, applying a powder to said charged surface forming a powder pattern on said charged surface, said powder ranging in particle size from submicron to about 45 microns, said pattern being a delineation of the ion-implanted structure in said crystal.

2. The process according to claim 1 wherein said material to be ionized is carbon and said implanting ions are ions of carbon.

3. The process according to claim 1 wherein said material to be ionized is boron and said implanting ions are ions of boron.

4. The process according to claim 1 wherein said material to be ionized is phosphorus and said implanting ions are ions of phosphorus.

5. The process according to claim 1 wherein said crystal is electrostatically charged and said powder is applied simultaneously.

6. The process according to claim 1 wherein said external surface is mechanically polished before said crystal is electrostatically charged.

7. The process according to claim 1 wherein said powder has a particle size ranging from submicron to about 5 microns.

8. The process according to claim 1 wherein said powder is selected from the group consisting of an insulating powder, a semiconducting powder and a metallic powder.

9. A fingerprint of a crystal selected from the group consisting of natural diamond, synthetic diamond and cubic boron nitride, said crystal having at least one external pattern producing surface with a surface area of at least 0.1 square millimeter which is at least substantially smooth said pattern producing surface being associated with a fingerprinting structure comprised of implanted ions, said fingerprint being composed of a powder pattern produced by the process of claim 1.

10. A photograph of the fingerprint of said crystal of claim 9.

11. The fingerprint of said crystal of claim 9 wherein said powder pattern is adhered to the adhesive surface of a transparent tape.

12. The fingerprint of said crystal of claim 9 wherein said powder ranges in particle size from submicron to 5 microns.

* * * * *